United States Patent

Genard et al.

[11] Patent Number: 5,871,755
[45] Date of Patent: Feb. 16, 1999

[54] DEHYDROALANINE DERIVATIVES FOR PROTECTING THE SKIN, THE MUCOUS MEMBRANES AND/OR THE HAIR FROM OXIDATIVE STRESS, COSMETIC OR DERMATOLOGICAL COMPOSITIONS CONTAINING THEM

[75] Inventors: Sylvie Genard, Paris; Jean Baptiste Galey, Aulnay-sous-Bois; Michel Hocquaux, Paris, all of France

[73] Assignee: L'Oreal, Paris, France

[21] Appl. No.: 529,049

[22] Filed: Sep. 15, 1995

[30] Foreign Application Priority Data

Sep. 15, 1994 [FR] France .................................. 94 11029

[51] Int. Cl.[6] .................................................... A61K 7/48
[52] U.S. Cl. ........................ 424/401; 424/701; 424/450; 514/844; 514/845; 514/846; 514/944; 560/169; 562/444; 562/449; 562/569
[58] Field of Search ...................... 424/401, 701, 424/450; 514/844–846, 944; 560/169; 562/444, 449, 569

[56] References Cited

FOREIGN PATENT DOCUMENTS 0113330  7/1984  European Pat. Off. .
1354571  6/1974  United Kingdom .

OTHER PUBLICATIONS

Buc–Calderon et al, "Inhibition of O2.–AND HO. –mediated processes by a new class of free radical scavengers; the N–acyldehydroalanines", Free Rad. Res. Comms., vol. 5, No. 3, 1988, pp.159–168.
Brandt et al, "Synthesis of Bis and Tris (dehydroalanine) Crosslinking Agents and Their Use in the Preparation of Hydrophilic Nucleic Acid Base Resins", Journal of Polymer Science: Part C: Polymer Letters, vol. 24, 1986, pp. 199–206.
Stella et al, "Stabilization of Radicals by 'Capto–Dative' Substitution –C–C Additoin to Radicophilic Olefins", Angew. Chem. Int. Ed. Engl., 17 (1978) No. 9, p. 691.

Primary Examiner—Jyothsna Venkat
Attorney, Agent, or Firm—Pillsbury Madison & Sutro LLP

[57] ABSTRACT

The present invention relates to the use of dehydroalanine derivatives of formula (I)

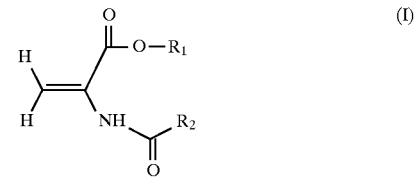

with $R_1$: H or linear- or branched-chain $C_1$–$C_4$ alkyl,

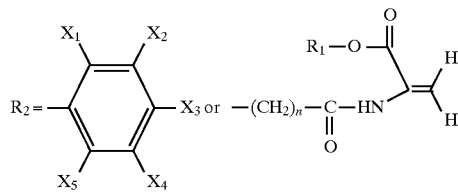

or linear- or branched-chain $C_1$–$C_{20}$ alkyl where $X_1$, $X_2$, $X_3$, $X_4$ and $X_5$=H, halogen, hydroxyl, linear-or branched-chain $C_1$–$C_4$ alkyl or alkoxy,

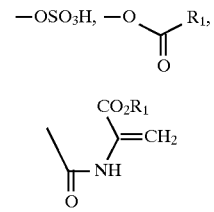

and n=2, 3 or 4, for protecting the skin, the mucous membranes and/or the hair against oxidative stress and to the cosmetic and dermatological compositions containing such compounds and to new dehydroalanine derivatives.

14 Claims, No Drawings

DEHYDROALANINE DERIVATIVES FOR PROTECTING THE SKIN, THE MUCOUS MEMBRANES AND/OR THE HAIR FROM OXIDATIVE STRESS, COSMETIC OR DERMATOLOGICAL COMPOSITIONS CONTAINING THEM

The present invention relates to dehydroalanine derivatives which are useful for protecting the skin, the mucous membranes and/or the hair against oxidative stress and to the cosmetic or dermatological compositions containing such compounds.

In the field of health and cosmetics, the concept of oxidative stress is known, which oxidative stress appears in particular as soon as a disequilibrium exists in the antioxidant/prooxidant balance. This imbalance is reflected in particular in uncontrolled oxidative processes within living tissues; these processes involve oxygenated free radicals and lead in particular to oxidative damage to biological molecules and macromolecules (Sies, H., in Oxidative Stress, Academic Press Inc. (London) Ltd., 1985).

It is known that various situations cause, promote or accompany oxidative stress or are the consequence thereof; they are in particular exposure to ultraviolet radiation and to ionizing radiation, aging, carcinogenesis, or the toxicity and/or method of action of certain medicaments.

Oxygenated free radicals are very unstable and very reactive species. Thus, in biological media, they react with all types of nearby molecules or macromolecules (sugars, proteins, lipids, nucleotides and the like) causing the oxidative damage mentioned above.

In order to protect biological tissues from this irreversible damage, a number of strategies can be envisaged. It is possible, for example, to act on one of the stages of formation of the oxygenated free radicals. It is also possible to envisage protecting biological tissues by stabilizing these activated oxygen species. This concept is, for example, illustrated by the theory of so-called captodative molecules.

According to this theory, since carbocations are stabilized by electron-donating substituants and carbanions are stabilized by electron-withdrawing substituents, it is possible to imagine the stabilization of radical centres substituted both by an electron-with-drawing substituent and by an electron-donating substituent. The molecules thus substituted are known as captodative molecules.

This theory has been, for example, confirmed for the captodative molecules of formula (II) when brought together with the isobutyronitrile radical (L. Stella, Z. Janousek, R. Merenyi, H. G. Viehe, Angew. Chem. Int. Ed. Engl., 1978, 17, 691)

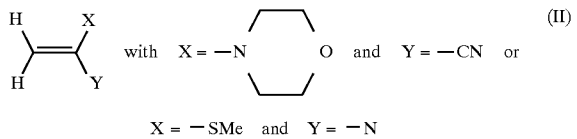

Other olefins of type (II) have been much studied for their radicophilic properties with respect to oxygenated radicals.

Thus, N-acyldehydroalanines, which are captodative dative molecules of formula (III):

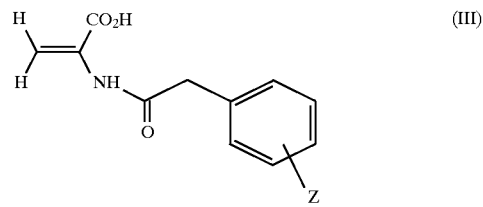

where Z=H or —OMe, for example, having been studied for their radicophilic properties with respect to oxygenated radicals. Reference may be made, in this respect, to the article by P. Buc-Calderon and M. Roberfoid, Free Rad. Res. Commun., 1988, 5, 159–68.

These molecules (III) have, in addition to the captodative site, two sites capable of reacting with oxygenated radicals: a proradical site (reactivity by abstraction of hydrogen) and an aromatic ring (addition of $OH°$):

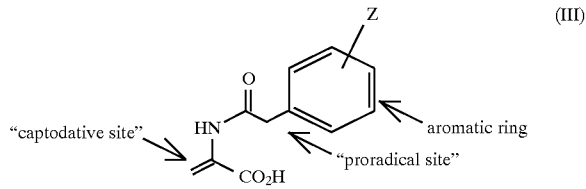

The compounds of formula (III) are used, for example, in the prevention and treatment of cancers, as described in the document EP-A-113,330.

Surprisingly, it has now been discovered that the compounds defined by the formula (I) below:

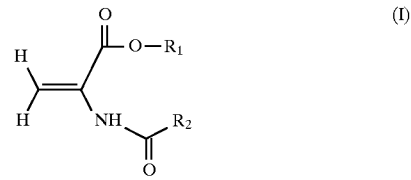

with $R_1$: H or linear- or branched-chain $C_1$ to $C_4$ alkyl,

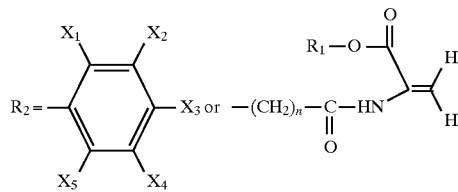

or linear- or branched-chain $C_1$–$C_{20}$ alkyl where $X_1$, $X_2$, $X_3$, $X_4$ and $X_5$=H, halogen, hydroxyl, linear- or branched-chain $C_1$–$C_4$ alkyl or alkoxy,

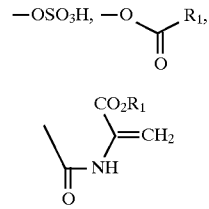

and n =2, 3 or 4, and their salts (when $R_1$=H) containing nontoxic cations, including alkali metal and alkaline-earth metal cations, such as sodium, lithium, potassium, calcium or magnesium, and ammonium salts,

3 had the property of protecting biological media in oxidative stress situations as efficiently as the dehydroalanines of formula (III), and even more efficiently at low concentration. This is all the more surprising since it might have been thought that the presence of the methylene group in the dehydroalanines of formula (III) was essential in the sense that it creates, in addition to that constituted by the double bond, an additional site which makes it possible to scavenge free radicals, as indicated in the article by Buc-Calderon mentioned above.

In the compounds of formula (I), the halogen is preferably chlorine but can also be bromine or fluorine. The $C_1$–$C_4$ alkyl or alkoxy radicals are preferably methyl, ethyl, methoxy or ethoxy. The $C_1$–$C_{20}$ alkyl radicals are preferably hexyl, heptyl, octyl, decyl, tetradecyl and octadecyl radicals.

The compounds of formula (I) have an excellent protective activity, with respect to cultured cells subjected to oxidative stress, at relatively low concentrations. Some of these compounds are active at a concentration of 0.1 $\mu$M, at which concentration they have a better protective activity than an N-acyldehydroalanine of formula (III) in which Z=—OCH, in the para position.

The compounds of formula (I) can therefore advantageously be used at low concentration, which has the advantage of thus minimizing the possible side effects of these compounds because it is known that the activity of a compound is always related to a certain degree of toxicity.

The subject of the present invention is thus a process for protecting the skin, the hair and/or the mucous membranes against oxidative stress which comprises administering topically to the skin, mucous membranes and/or hair an effective amount of the dehydroalanine derivatives of formula (I) above.

Another subject is constituted by the cosmetic or dermatological compositions using these compounds.

Some compounds among the dehydroalanines of formula (I) are novel. It concerns the compounds of general formula:

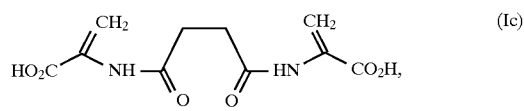

(Ia)

in which
$R_1$ denotes hydrogen,
X denotes a halogen,
R denotes a linear- or branched-chain $C_1$–$C_4$ alkyl radical,
n+m=1 to 5, it being possible for m to be zero,
p=0 or 1, ,
and their alkali metal or alkaline-earth metal or ammonium salts.

The methyl and ethyl radicals are preferred as R radicals.

The halogen atom X is preferably chlorine but can also denote bromine or fluorine.

Mention may also be made, among the new compounds of formula (I), of the compounds of following formula (Ib):

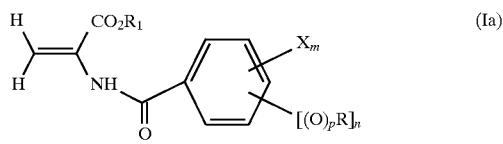

(Ib)

with n=2, 3 or 4 and $R_1$=H or linear- or branched-chain $C_1$–$C_4$ alkyl, in particular of the dehydroalanine derived from succinamide having the following formula:

4

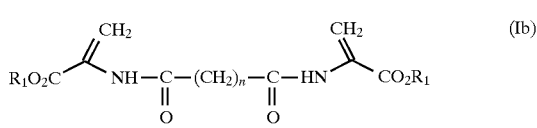

(Ic)

and of their alkali metal or alkaline-earth metal or ammonium salts.

Another subject of the invention is therefore the new compounds of formulae (Ia) and (Ib) above.

The dehydroalanines of formulae (I), (Ia) and (Ib) are prepared according to a process chosen from the processes mentioned in the literature for the preparation of compounds of this type. It is possible to prepare them, for example, by condensing an appropriate amide with pyruvic acid or its ester, at reflux of a suitable organic solvent, as described in the documents Bull. Acad. Sci. USSR, 1955, p. 231 or Chem. Ber. 1957, volume 90, p. 194; or else by passing through an intermediate chloramine derived from alanine, as described, for example, in the document Synthesis, 1977, p. 457; or alternatively by passing through an intermediate chloramine derived from aspartic acid or from its ester, as described, for example, in the document Agric. Biol. Chem., 1984, volume 48, p. 1251–5; or alternatively by dehydration of serine derivatives, either by carbonyldiimidazole, as described, for example, in Synthesis, 1982, p. 968, or by various carbodiimides, as described, for example, in the document J. Org. Chem., 1980, volume 45, p. 3131–2, or by formation of a mesylate group which can be split off, as described, for example, in the document Bull. Chem. Soc. Jpn., 1981, volume 54, p. 1132, or of a tosylate group which can be split off, as described, for example, in J. Am. Chem. Soc., 1963, volume 85, p. 1123; or finally by dehydrohalogenation of β-chloroalanines, as described, for example, in the document J. Polym. Sci., Part C: Polym. Lett., 1986, 24, 199.

Other subjects of the invention will become apparent on reading the description and examples which follow.

The following examples illustrate the processes for the preparation of the new compounds of formulae (Ia) and (Ib).

EXAMPLES

Example 1

Preparation of N-(ortho-toluyl)dehydroalanine (2-stage synthesis)

1st Stage:

20 g of DL-aspartic acid (Aldrich) are dissolved in 210 ml of a 2.5N aqueous sodium hydroxide solution (120 ml)/THF (90 ml) mixture in a 500 ml, three-necked, round-bottomed flask equipped with a pHmeter and two dropping funnels containing, on the one hand, a 2.5N aqueous sodium hydroxide solution and, on the other hand, o-toluyl chloride. The o-toluyl chloride is added drop-wise while maintaining the pH above 9 by simultaneous addition of the 2.5N sodium hydroxide solution. The reaction mixture is kept stirring for 2 h 30 minutes after the end of the addition of the acid chloride before being acidified with a concentrated hydrochloric acid solution. The mixture is then exhaustively extracted with ethyl acetate. The organic phase is washed, dried and concentrated to dryness to provide 27.9 g (non-optimized yield 74%) of N-(ortho-toluyl)aspartic acid, used as is in the second stage.

$^1$H NMR 400 MHz ($d_6$-DMSO, δ ppm): 2.34 (s, 3H, $CH_3$), 2.67 (d.d, 1H, H2a), 2.82 (d.d, 1H, H2b), 4.72 (m, 1H, H3), 7.23 (m, 2H, H8 and H10), 7.31 (m, 2H, H9 and H11), 8.48 (d, 1H, H4), 12.53 (s, 2H, OH).

$^{13}$C NMR 100 MHz (d$_6$-DMSO, δ ppm): 19.18 (CH$_3$), 35.75 (C2), 49.01 (C3), 125.35 (C10), 126.99 (C11), 129.34 (C8), 130.33 (C9), 135.30 (C6), 136.58 (C7), 168.83 (C5), 171.68 (C1 or C12), 172.39 (C1 or C12).

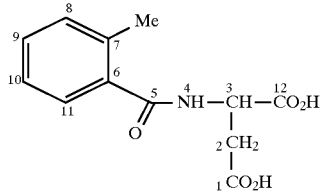

Elemental analysis:

|  | C % | H % | N % | O % |
| --- | --- | --- | --- | --- |
| Calculated | 57.37 | 5.22 | 5.58 | 31.84 |
| Found | 57.21 | 5.01 | 5.37 | 31.82 |

Melting point: 160° C. (Kofler)

2nd Stage:

10 g of N-(ortho-toluyl)aspartic acid are disolved in 20 ml of methanol in a 500 ml, three-necked, round-bottomed flask equipped with a thermometer, a dropping funnel and a reflux condenser. After having completely dissolved, 28.5 ml of an aqueous sodium hypochlorite solution, assaying at 1.40 mol/l, are added dropwise while maintaining the temperature below 20 °C. At the end of the addition, the mixture is diluted with 180 ml of methanol before being brought to reflux for 1 h 30 minutes. After concentrating under vacuum, the residue is taken up in ethyl acetate and extracted with an aqueous sodium bicarbonate solution. The aqeuous phase is acidified with hydrochloric acid and extracted with ethyl acetate. The organic phase is washed with brine before being dried and concentrated under vacuum to provide an oil which crystallizes on addition of water. The precipitate formed is filtered and purified by recrystallization from water (a few drops of methanol are added, if necessary) to provide 2.65 g of N-(ortho-toluyl) dehydroalanine. (Nonoptimized yield 32%).

$^1$H NMR 500 MHz (d$_6$-DMSO, δppm): 2.38 (s, 3H, H12), 5.77 (s, 1H, H11b), 6.13 (s, 1H, H11a), 7.26 to 7.32 (m, 2H, H3 and H5), 7.37 to 7.40 (t.d, 1H, H4), 7.40 to 7.45 (d.d, 1H, H6), 9.23 (s, 1H, NH), 13.28 (s, 1H, H10).

$^{13}$C NMR 125 MHz (d$_6$-DMSO, δppm): 19.42 (C12), 109.81 (C11), 125.68 (C5), 127.12 (C6), 130.00 (C4), 130.71 (C3), 133.93 (C9), 135.64 (C2), 135.91 (C1), 165.03 (C10), 167.90 (C7).

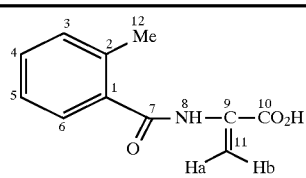

Elemental analysis:

|  | C % | H % | N % | O % |
| --- | --- | --- | --- | --- |
| Calculated | 64.38 | 5.40 | 6.83 | 23.39 |
| Found | 64.33 | 5.45/5.36 | 6.80 | 23.27 |

Melting point: 108° C. (Kofler)

Example 2

Preparation of N-(2-methoxy-5-chlorobenzoyl) dehydroalanine (2-stage synthesis)

1st Stage:

10 g of DL-aspartic acid (Aldrich) are dissolved in 105 ml of a 2.5N aqueous sodium hydroxide solution (60 ml)/THF (45 ml) mixture in a 500 ml, three-necked, round-bottomed flask equipped with a phmeter and with two dropping funnels containing, on the one hand, a 2.5N aqueous sodium hydroxide solution and, on the other hand, 2-methoxybenzoyl chloride. The 2-methoxybenzoyl chloride is added dropwise while maintaining the pH above 9 by simultaneous addition of the 2.5N sodium hydroxide solution. The reaction mixture is kept stirring for 3 h after the end of the addition of the acid chloride before being acidified with a concentrated hydrochloric acid solution. The mixture is exhaustively extracted with ethyl acetate. The organic phase is washed, dried and concentrated to dryness to provide crude N-(2-methoxybenzoyl) aspartic acid. The product can be used as is in the second stage (nonoptimized yield 75%) or purified by washing with a suitable organic solvent. $^1$H NMR 500 MHz (d$_6$-DMSO, δppm): 2.83 (m, 2H, H9), 3.92 (s, 3H, H12); 4.80 (m, 1H, H8), 7.07 (d.d.d, 1H, H4), 7.18 (d.d, 1H, H2), 7.52 (d.d.d, 1H, H3), 7.91 (d.d, 1H, H5), 8.85 (d, 1H, NH), 12.68 (s, 2H, OH).

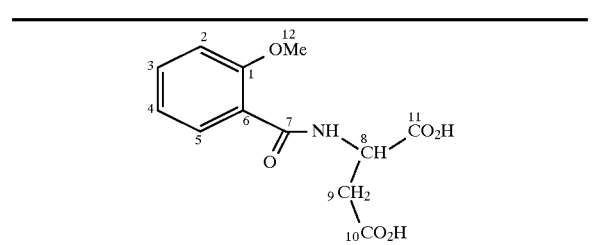

Mass: MH$^+$ = 268
Elemental analysis:

|  | C % | H % | N % | O % |
| --- | --- | --- | --- | --- |
| Calculated | 53.95 | 4.90 | 5.24 | 35.92 |
| Found | 53.98 | 4.95 | 5.15 | 35.80 |

Melting point: 196° C. (Kofler)

2nd Stage:

The N-(2-methoxybenzoyl)aspartic acid is dissolved solved in methanol (2.7 ml/g) in a reactor equipped with a thermometer, a dropping funnel and a reflux condenser. After having completely dissolved, an assayed aqueous sodium hypochlorite solution is added dropwise while maintaining the temperature below 20°C. At the end of the addition, the mixture is diluted twofold with methanol before being brought to reflux for 1 h 30 minutes. After concentrating under vacuum, the residue is taken up in ethyl acetate and extracted with an aqueous sodium bicarbonate solution. The aqueous phase is acidified with hydrochloric acid and extracted with ethyl acetate. The organic phase is washed with brine before being dried and concentrated under vacuum. The residue is dissolved at reflux in a 1/1 ethanol/water mixture. N-(2-Methoxy-5- chlorobenzoyl) dehydroalanine crystallizes on cooling. (Nonoptimized yield 4%). $^1$H NMR 500 MHz (d$_6$-DMSO, δppm) : 4.02 (s, 3H, H12), 5.82- 6.58 (s, 2H, H11), 7.30 (d, 1H, H6), 7.63 (d.d, 1H, H5), 7.94 (d, 1H, H3), 10.48 (s, 1H, NH), 13.68 (s, 1H, H10).

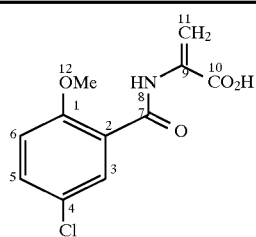

Mass: M⁺ = 255
Elemental analysis:

|  | C % | H % | N % | O % | Cl % |
|---|---|---|---|---|---|
| Calculated | 51.68 | 3.94 | 5.48 | 25.03 | 13.87 |
| Found | 52.38 | 4.05 | 5.56 | 25.24 |  |

Melting point: 210–214° C. (Kofler)

Example 3

Preparation of N-(2-methoxybenzoyl) dehydroalanine (1-stage synthesis)

A suspension of 2-methoxybenzamide in 1,2-dichloroethane (24.5 ml/g) is brought to reflux in the presence of 3 equivalents of freshly distilled pyruvic acid in a round-bottomed flask surmounted by a system which makes it possible to remove the water formed during the reaction. When the formation of water has finished (approximately 7 hours), the reaction mixture is left at room temperature. After filtering off the insoluble materials, the filtrate is extracted with an aqueous sodium bicarbonate solution. The combined aqueous phases are extracted with dichloromethane and then acidified with hydrochloric acid. The precipitate formed is filtered off, dried and then taken up in ethyl acetate. After filtering off the insoluble material, the filtrate is concentrated under vacuum, dissolved in dichloromethane and then precipitated with heptane, thus providing pure N-(2-methoxybenzoyl)dehydroalanine. (Nonoptimized yield 8.5%).

$^{1}$H NMR 500 MHz (d$_{6}$-DMSO, δ ppm): 4.01 (s, 3H, H12), 5.79 (s, 1H, H11a), 6.59 (s, 1H, H11b), 7.12 to 7.15 (d.d, 1H, H4), 7.25 to 7.26 (d.d, 1H, H6), 7.57 to 7.59 (d.d, 1H, H5), 8.01 to 8.03 (d.d, 1H, H3), 10.54 (s, 1H, NH), 13.66 (s, 1H, OH).

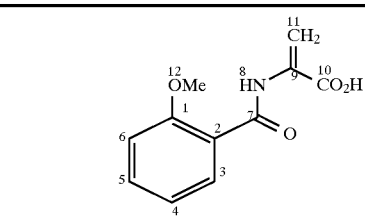

Elemental analysis:

|  | C % | H % | N % | O % |
|---|---|---|---|---|
| Calculated | 59.73 | 5.01 | 6.33 | 28.93 |
| Found | 59.72 | 5.07 | 6.46 | 28.85 |

Melting point: 132° C. (Kofler)

Example 4

Dehydroalanine derived from succinamide (Compound Ic)

A suspension of succinamide in toluene (30 ml/g) is brought to reflux in the presence of 6 equivalents of freshly distilled pyruvic acid in a round-bottomed flask surmounted by a Dean and Stark apparatus and a reflux condenser. When the formation of water has finished (approximately 5 hours), the reaction mixture is extracted with an aqueous sodium bicarbonate solution. The aqueous phase is acidified with concentrated hydrochloric acid in order to precipitate the dehydroalanine. After filtration, the solid dehydroalanine is copiously washed with an ethanol/acetone mixture and then twice with methyl acetate before being dried under vacuum in a desiccator (Nonoptimized yield 2.3%).

$^{1}$H NMR 500 MHz (d$_{6}$-DMSO, δ ppm): 2.59 (s, 4H, H5 & 5'), 5.66 (s, 2H, H2a & H2'a), 6.24 (s, 2H, H2b & H2'b), 9.09 (s, 2H, H3 & H3') 13.26 (s, 2H, H1 & H1').

$^{13}$C NMR 100 MHz (d$_{6}$-DMSO, δ ppm): 30.94 (C$_{5}$, C$_{5}$), 107.51 (C$_{2}$, C$_{2}$,), 133.06 (C$_{6}$, C$_{6}$,), 164.86 (C$_{1}$ and C$_{1}$, or C$_{4}$ and C$_{4}$,), 171.16 (C$_{1}$ and C$_{1}$, or C$_{4}$ and C$_{4}$,).

Elemental analysis:

|  | C % | H % | N % | O % |
|---|---|---|---|---|
| Calculated | 46.88 | 4.72 | 10.93 | 37.47 |
| Found | 46.34/46.46 | 4.90/5.0 | 10.57/10.54 | 36.50/36.36 |

Melting point: greater than 250° C. (Kofler)

The compounds of formulae (I), (Ia) and (Ib) and their salts can be used in cosmetic or dermatological compositions for protecting the skin from oxidative stress.

The cosmetic or dermatological compositions according to the invention are those conventionally used in the cosmetics or dermatological fields and can be, for example, in the form of water-in-oil or oil-in-water emulsions, of aqeuous, alcoholic or oily gels or aqueous, aqueous/alcoholic or alcoholic solutions, as a vesicular dispersion or in the form of foams or of sprays.

The cosmetic or dermatological compositions according to the invention use the compounds of formulae (I), (Ia) and (Ib) or their salts, in a cosmetically or dermatologically acceptable medium.

These compositions contain the compounds of formulae (I), (Ia) and (Ib) in proportions ranging from 0.001 to 10 weight % and preferably from 0.01 to 2 weight %.

The cosmetically or dermatologically acceptable medium is a medium usual in the cosmetic or dermatological field.

The cosmetic or dermatological compositions containing the compounds of formulae (I), (I*a*) or (I*b*) can in particular comprise cleaning, protection, treatment or care creams for the face, for the hands or for the body (for example day creams, night creams, make-up removal creams, foundation creams or anti-sun creams), liquid foundations, make-up removal milks, protection or care body milks, anti-sun milks, lotions, gels or foams for caring for the skin, such as cleaning lotions, anti-sun lotions, artificial tanning lotions, hair care compositions, and in particular shampoos, styling creams or gels, lotions or gels for combating hair loss, and the like.

In a known way, the compositions of the invention can contain, in addition to hydrophilic or lipophilic active agents, adjuvants usual in the cosmetics or dermatological field, such as hydrophilic or lipophilic gelling agents, preservatives, solvants, fragrances, fillers and colouring materials. The amounts of these various adjuvants are those conventionally used in the cosmetics or dermatological field.

The cosmetic or dermatological compositions according to the invention can contain, in addition to the compounds of formulae (I), (Ia) and (Ib), at least one cosmetic or dermatological active principle chosen more particularly from antiinflammatories, antiacne agents, antipsoriatic agents, antifungal agents, antibacterial agents, agents for combating hair loss, antidandruff agents, screening agents, vitamins, keratolytic agents, antioxidants, humectants, agents for combating free radicals other than the compounds (I), (Ia) and (Ib), and the like.

The following examples illustrate the cosmetic and dermatological compositions according to the invention

EXAMPLES

Example 1

The following composition is prepared:

| | | |
|---|---|---|
| Propylene glycol | | 45.00 g |
| N-Benzoyldehydroalanine | | 1.00 g |
| Clucel H (hydroxypropylcellulose) | | 1.50 g |
| Anhydrous ethanol | q.s. for | 100 g |

Example 2

The following composition is prepared:

| | | |
|---|---|---|
| Glyceryl monostearate | | 0.80 g |
| Cetyl alcohol | | 2.00 g |
| Cetylstearyl alcohol | | 5.00 g |
| Polyoxyethylene stearate (sold under the name of "Myrj 49") | | 3.00 g |
| Acrylic acid crosslinked by a polyfunctional agent (sold under the name of "Carbopol 941") | | 0.50 g |
| Triethanolamine | | 0.30 g |
| Miglyol 812 | | 12.00 g |
| Preservative | q.s. | |
| N-Benzoyldehydroalanine | | 0.5 g |
| Water | q.s. for | 100 g |

This composition is provided in the form of a cream intended to be applied topically to the area of the skin to be protected.

In the claims:

1. Process for protecting the skin, mucous membranes and hair against oxidative stress which comprises administering topically to the skin, mucous membranes and hair an effective amount of a dehydroalanine of formula (I)

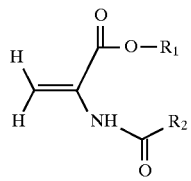

wherein $R_1$ denotes hydrogen or linear- or branched-chain $C_1$–$C_4$ alkyl, $R_2$ denotes linear- or branched-chain $C_1$–$C_{20}$ alkyl or has the formula:

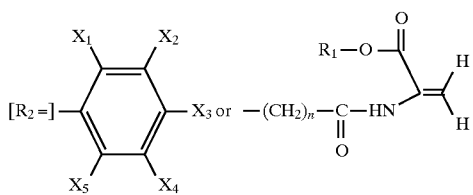

wherein $X_1$, $X_2$, $X_3$, $X_4$, and $X_5$ denote H, halogen, hydroxyl, linear- or branched-chain $C_1$–$C_4$ alkyl or alkoxy, —$OSO_3H$,

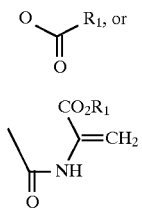

$R_1$ has the above meaning and n=2, 3 or 4, or of its alkali metal or alkaline-earth metal or ammonium salts.

2. Process according to claim 1 wherein in the compound of formula (I), the halogen represented by $X_1$, $X_2$ $X_3$, $X_4$ and $X_5$ is chlorine.

3. Process according to claim 1 wherein in the compound of formula (I), the $C_1$–$C_4$ alkyl or alkoxy radical is selected from the group consisting of methyl, ethyl, methoxy and ethoxy radicals.

4. Cosmetic or dermatological composition, which contains an effective amount of at least one compound of formula (I) as defined in claim 1 in a cosmetically or dermatologically acceptable medium.

5. Composition according to claim 4, which contains 0.0001 weight % to 10 weight % of at least one compound of formula (I) as defined in claim 1.

6. Composition according to claim 5, which contains 0.01 weight % to 2 weight % of at least one compound of formula (I) as defined in claim 1.

7. Composition according to claim 4, which comprises at least one compound of formula (I) selected from the group consisting of N-benzoyldehydroalanine, N-(ortho-toluyl) dehydroalanine, N-(2-methoxy-5-chloroalanine and the dehydroalanine derived from succinamide corresponding to the formula:

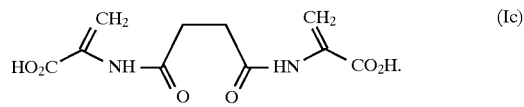

8. Cosmetic or dermatological composition according to claim 4, which further contains at least one cosmetic or dermatological active principle selected from the group consisting of antiinflammatories, antiacne agents, antipsoriatic agents, antifungal agents, antibacterial agents, agents for combating hair loss, antidandruff agents, screening agents, vitamins, keratolytic agents, humectants, agents for combating free radicals other than those of formula (I), and antioxidants.

9. Dehydroalanine derivative of formula:

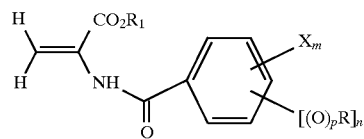
(Ia)

wherein
$R_1$ denotes hydrogen,
X denotes a halogen,
R denotes a linear- or branched-chain $C_1$–$C_4$ alkyl radical,
n+m=1 to 5, it being possible for m to be zero,
p=0 or 1,
or its alkali metal or alkaline-earth metal or ammonium salts.

10. Dehydroalanine derivative according to claim 8, wherein R denotes a methyl or ethyl radical.

11. Dehydroalanine derivative according to claim 8 wherein the halogen X is chorine.

12. Dehydroalanine derivative according to claim 8, which is selected from the group consisting of N-(ortho-toluyl) dehydroalanine, N-(2-methoxy-5-chlorobenzoyl) dehydroalanine and N-(2-methoxybenzoyl) dehydroalanine.

13. Dehydroalanine derivative of formula:

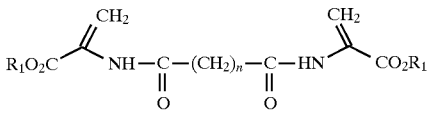
(Ib)

wherein
n=2, 3 or 4,
$R_1$=H or linear-or branched-chain $C_1$–$C_4$ alkyl,
or its alkali metal or alkaline-earth metal or ammonium salts.

14. Dehydroalanine derivative according to claim 12, wherein $R_1$ denotes hydrogen and n is equal to 2.

* * * * *